United States Patent [19]
Mortimer

[11] Patent Number: 5,987,361
[45] Date of Patent: Nov. 16, 1999

[54] POLYMER-METAL FOIL STRUCTURE FOR NEURAL STIMULATING ELECTRODES

[75] Inventor: J. Thomas Mortimer, Chagrin Falls, Ohio

[73] Assignee: Axon Engineering, Inc., Cleveland, Ohio

[21] Appl. No.: 08/849,774

[22] PCT Filed: Mar. 7, 1997

[86] PCT No.: PCT/US97/03423

§ 371 Date: Nov. 13, 1998

§ 102(e) Date: Nov. 13, 1998

[87] PCT Pub. No.: WO97/32628

PCT Pub. Date: Sep. 12, 1997

Related U.S. Application Data

[60] Provisional application No. 60/012,962, Mar. 7, 1996.
[51] Int. Cl.[6] .................................................. A61N 1/05
[52] U.S. Cl. ............................ 607/118; 607/152; 29/825
[58] Field of Search ................................... 607/115, 116, 607/118, 127, 142, 137, 148, 152; 600/373, 372, 377; 29/825, 745, 746

[56] References Cited

U.S. PATENT DOCUMENTS

| | | |
|---|---|---|
| 4,763,660 | 8/1988 | Kroll et al. . |
| 4,940,065 | 7/1990 | Tanagho et al. ..................... 607/118 |
| 5,324,322 | 6/1994 | Grill, Jr. et al. . |

*Primary Examiner*—William E. Kamm
*Assistant Examiner*—George R. Evanisko
*Attorney, Agent, or Firm*—Fay, Sharpe, Fagan, Minnich & McKee, LLP

[57] ABSTRACT

A neural stimulating electrode structure includes a sheet of metal foil having portions defining holes. The holes form patterns allowing the metal foil to flex without buckling when subjected to compressive forces. The holes also define discrete electrodes on the metal foil when the foil is cut. A first polymeric base layer covers a first face of the metal foil. A second polymeric base layer covers a second face of the metal foil. The first and second polymeric base layers fill the holes in the metal foil. A third polymeric base layer covers both the first and second polymeric base layers. The third polymeric base layer has portions defining pairs of holes. Each pair of holes is associated with one of the discrete electrodes. Each hole exposes a different portion of the discrete electrode for contacting tissue, passing current and/or measuring voltage.

17 Claims, 7 Drawing Sheets

POLYMER-METAL FOIL STRUCTURE FOR NEURAL STIMULATING ELECTRODES

This application claims benefit of provisional application Ser. No. 60/012,962, filed Mar. 7, 1996.

BACKGROUND OF THE INVENTION

The present invention relates to the biomedical arts. It finds particular application in conjunction with cuff electrodes for stimulating nerves and will be described with particular reference thereto. It will be appreciated, however, that the present invention is also applicable to other types of implanted electrodes and biomedical devices.

Many types of nerve tissue damage do not heal. Such injuries leave a patient permanently without an appropriate nerve path for electrical signals or action potentials which travel from the brain to muscles or other biological tissue to cause a biological response. Similarly, such a discontinuity prevents action potentials from carrying sensory information or other biological feedback from the tissues to the brain. Moreover, there is also a tendency for action potentials to commence propagating naturally from below the injury site to the biological tissue causing an unconscious and unwanted biological response. Analogously, action potentials can propagate from above the injury site to the brain causing pain and erroneous sensory feedback.

Electrical potentials can be applied to nerve trunks and fibers to block the propagation of action potentials and for controllably initiating the propagation of action potentials in an upstream direction, a downstream direction, or both. Neural electrodes, such as illustrated in U.S. Pat. No. 4,602,624 to Naples, Sweeney, and Mortimer, and U.S. Pat. No. 5,324,322 to Grill, Jr., Creasey, Ksienski, Veraart and Mortimer controllably initiate and/or block action potentials in the nerves.

Although the prior art neural electrodes have proven effective, they do have drawbacks. Initially, certain types of prior art neural electrodes are labor intensive to manufacture, requiring the hand of a skilled fabricator to weld conducting wires to foil and fitting these foil conductors to silicone rubber coverings. Hand fabrication results in various problems, including the tendency of the foil conductors buckling when the metal-silicone structure is flexed. The flexure causes the foil to work harden and ultimately become a source for mechanical failure, stress corrosion, cracking and/or subsequent conduction failure.

Also, for neural electrodes whose patterns are formed with a metal deposition on a flexible substrate (e.g., silicone rubber or polyamide) there is a tendency for the metal to crack. The cracks on the surface appear as "cracked mud" at a microscopic level. Such cracks have the tendency to fill with uncured polymer when pressure is applied to a metal-polymer structure. This causes the uncontrolled formation of metal "islands," separated by the nonconducting polymer. Nonconducting polymer between "islands" eliminates electrical conduction along a trace by causing multiple open circuits.

The present invention provides a new and improved neural electrode and method of manufacture which overcomes the above-referenced problems and others.

SUMMARY OF THE INVENTION

A neural stimulating electrode comprises a sheet of metal foil having holes formed at predetermined locations. The holes are positioned to form patterns which allow the metal foil to flex without buckling when subjected to compressive forces. The holes also define a plurality of discrete electrodes on the metal foil when the foil is cut. A first polymeric base layer covers a first face of the metal foil. A second polymeric base layer covers a second face of the metal foil. The first and second polymeric base layers fill the holes in the metal foil. A third polymeric base layer covers both the first and second polymeric base layers. The third polymeric base layer has portions defining pairs of holes. Each pair of holes is associated with one of the discrete electrode structures. Each hole in each of the pairs of holes exposes a different portion of the discrete electrode structure for contacting tissue, passing current and/or measuring voltage.

In accordance with one aspect of the invention, the three polymeric base layers are laser cutable.

In accordance with another aspect of the invention, the three polymeric base layers are silicone rubber.

In accordance with another aspect of the invention, the neural stimulating electrode forms a curving surface for conforming to an outside surface of a nerve.

A principal advantage of the present invention is that voids formed in the metal foil filled with silicone rubber form islands of insulating material, which along with regions of conducting material create a continuous composite structure with a conducting surface that accommodates compression (i.e., bending) without buckling.

Another advantage of the present invention is that it reduces manual labor and manufacturing time.

Still another advantage of the present invention is that it facilitates automated, mass production techniques by using laser cutable materials (e.g., platinum or silicone rubber) along with chemical etchable materials.

Yet, another advantage of the present invention is that it facilitates implantation and interconnection with electrical leads.

Still yet another advantage of the present invention is that it prolongs electrode life.

A further advantage of the present invention is that the electrode is electrically insulated and more flexible than solid foil sheets sandwiched between two layers of polymer.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

FIG. 10 is a top elevational view of a completed electrode according to the second embodiment;

DETAILED DESCRIPTION OF THE PREFERRED EMBODIMENTS

Figure 1:
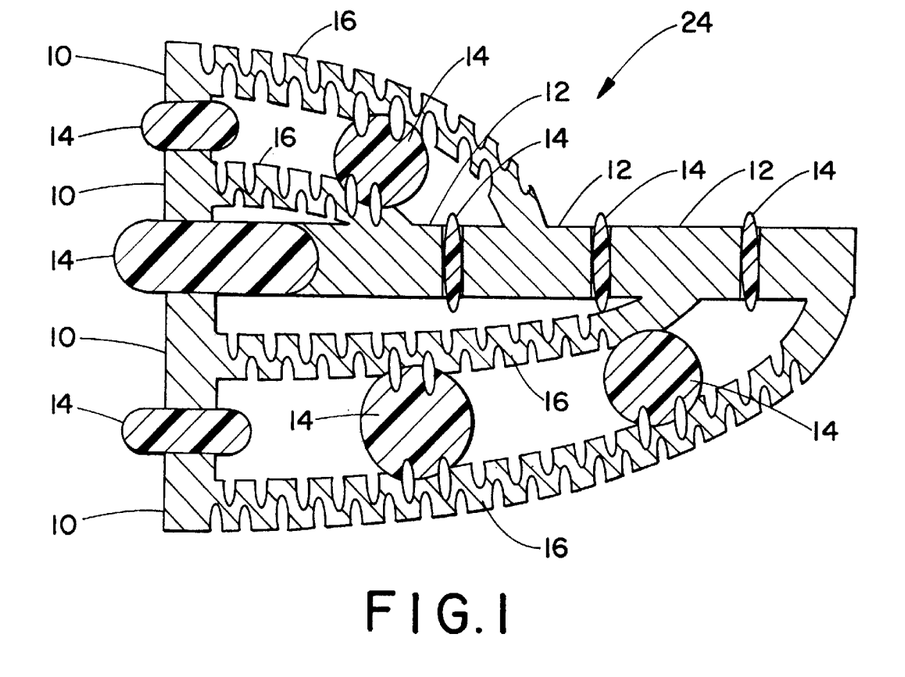
FIG. 1 is a top elevational view of an electrode construction in accordance with a first embodiment the present invention.
Figure 5:
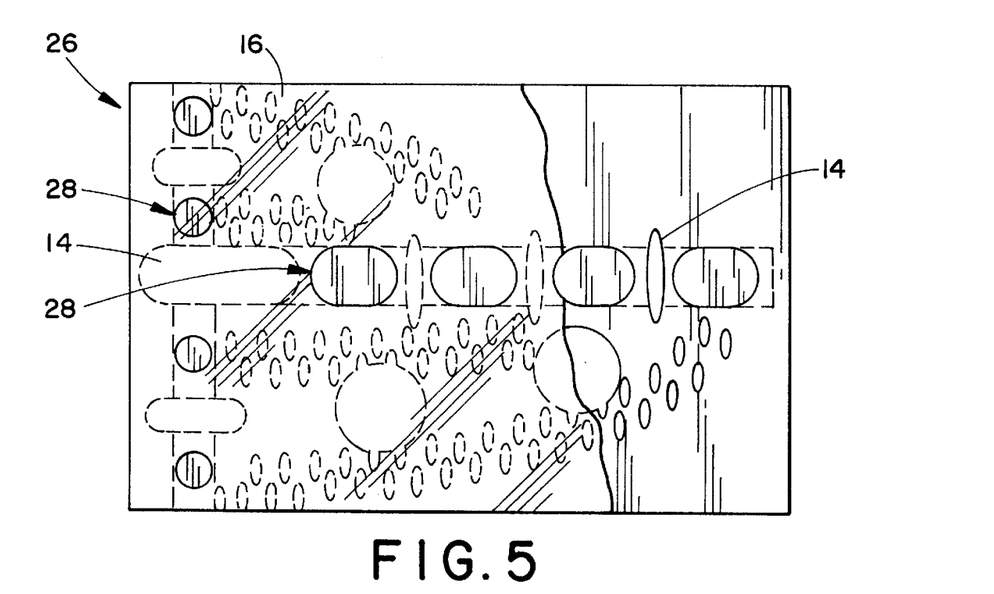
FIG. 5 is a top elevational view of a completed electrode according to the first embodiment.

FIG. 1 sets forth a cut-out trace of an electrode structure 24 (FIG. 5). The cut-out trace 24 includes a plurality of electrodes, each composed of a conductive path 16 connected to an electrical lead pad 10 at one end and an electrical connection portion 12 at a second end. A polymer 14 provides mechanical interconnections between the lead pads 10 and connection portions 12. It is also noted that in the preferred embodiment, the polymer is a laser cutable polymer.

Figure 2:
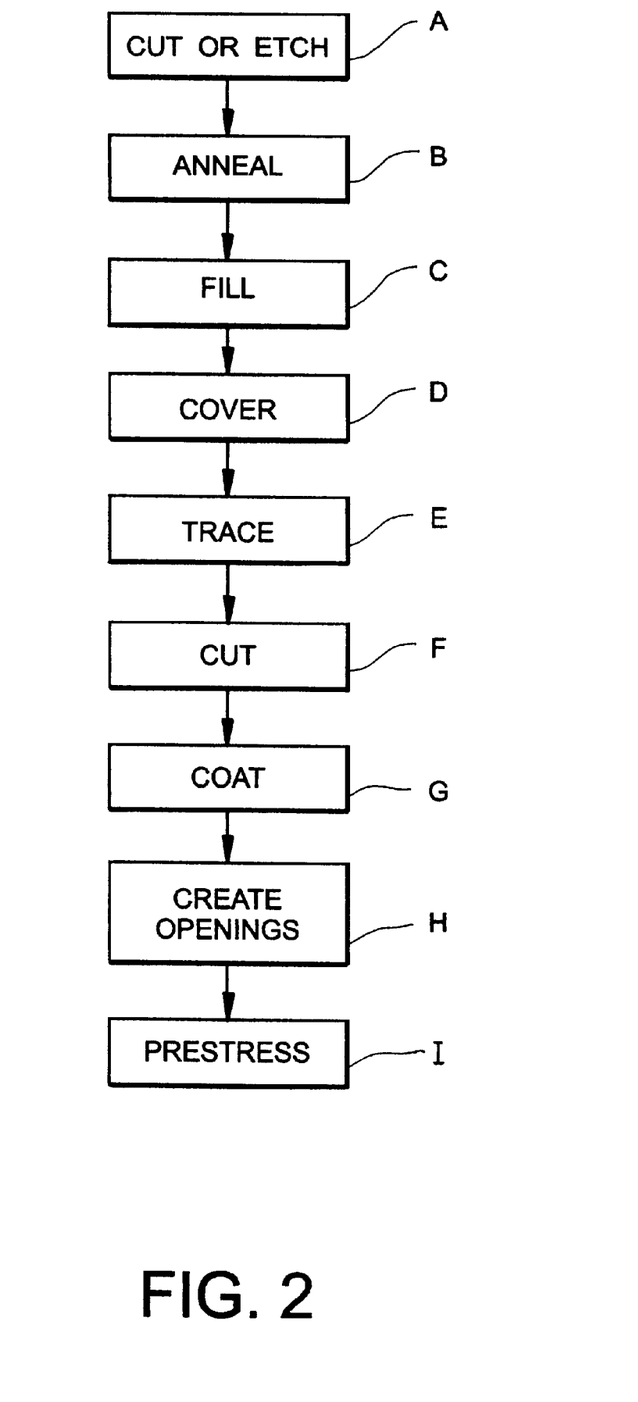
FIG. 2 is a flow chart for manufacturing an electrode in accordance with the present invention.
Figure 3A:
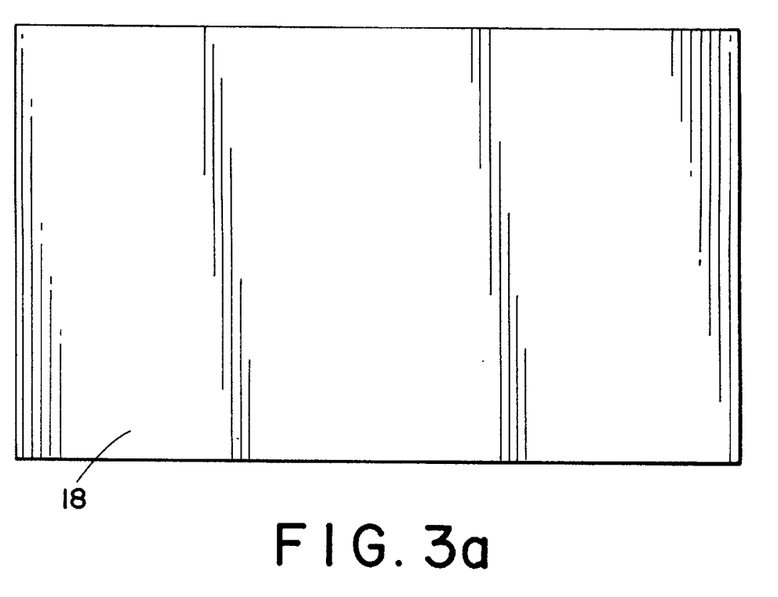
FIG. 3a is a top elevational view of sheet of metal foil.
Figure 3B:
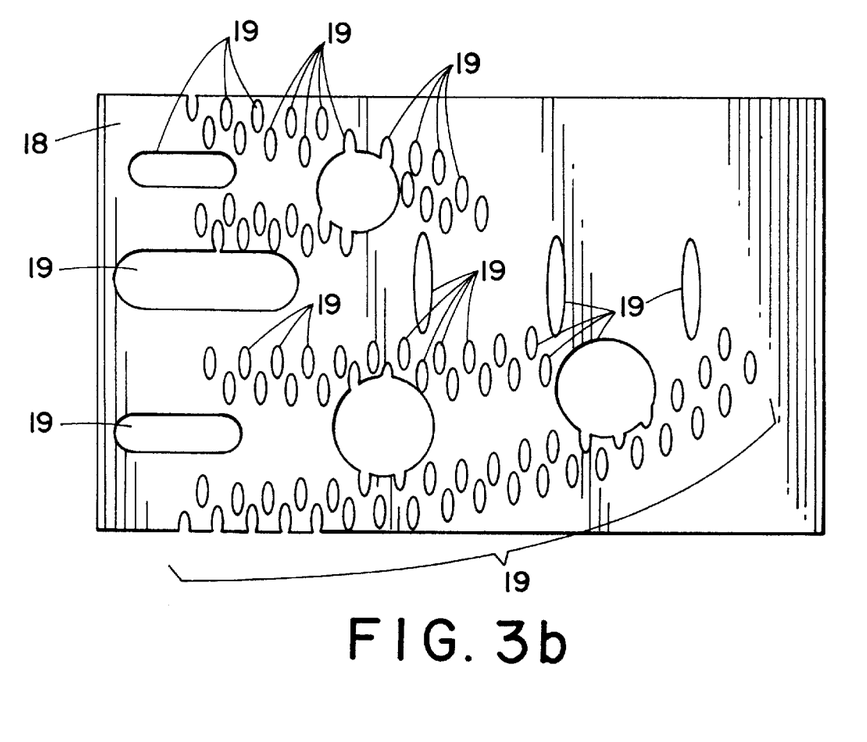
FIG. 3b is a top elevational view of a sheet of metal containing voids.

The construction of the electrode structure begins with a sheet of metal foil 18 (FIG. 3a). In the preferred embodiment, the thickness of the foil 18 is preferably between about 10 μm and about 75 μm. With reference to the flow chart of FIG. 2 and the illustration of FIG. 3b, holes 19 are cut or etched into the foil 18 in a cutting or etching step A. The holes 19 are cut to form patterns for creating the multiple electrodes within the foil sheet 18. If desired, residual internal stresses are then removed from the foil 18 in an annealing step B.

Figure 3C:
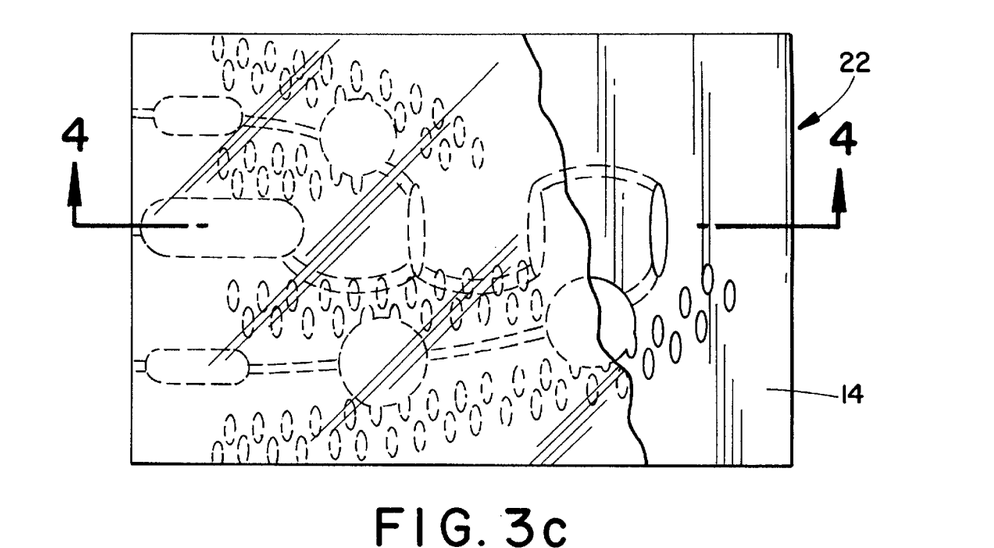
FIG. 3c is a top elevational view of a partially constructed electrode consisting of a metal sandwiched between two layers of a polymer.
Figure 4:
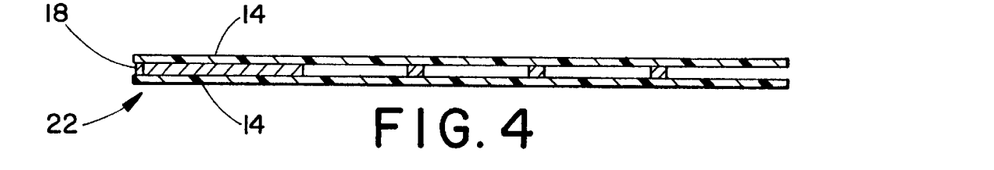
FIG. 4 is a cross-sectional side view of the polymer-metal-polymer structure shown in FIG. 3c.

Next, the laser cutable polymer 14 is introduced into the holes 19 of the metal foil 18 in a filling step C. The laser cutable polymer 14 is preferably silicone rubber. However, other materials with similar qualities are also contemplated. The resulting metal-polymer combination is then sandwiched between two layers of the polymer 14 in a covering step D to form a polymer-metal-polymer structure 22 (see FIGS. 3c and 4). It is appreciated that fill step C can be accomplished as part of course step D, and that when fill step C and cover step D are distinct steps, it is possible to use different polymers in steps C and D. The electrodes are then defined within the polymer-metal-polymer structure 22 in a tracing step E. The cut-out trace 24, having lead pads 10 and connection portions 12, is then created from the tracing in a cutting step F (see FIG. 1).

To complete the construction of the electrode structure 26, the cut-out trace 24 is laminated with an additional polymer layer or sheet of the laser cutable polymer 14 in step G to form a laminated sheet of electrodes 26 (see FIG. 5). Either one or both surfaces of cut-out trace 24 can be laminated. Alternatively, the cut-out trace 24 itself may be used or the cut-out trace 24 may be associated in some other manner to a non-conducive surface. Lead pads 10 and connection portions 12 are created in the electrode structure 26 in a create openings step H. Preferably, a laser cutting device is used to create the openings. However, the openings may also be created mechanically. The beam properties (e.g., intensity, wavelength, etc.) of the laser are adjusted so that the laser cutting device cuts through the laminated layer and polymer layer of step D while leaving the metal foil 18 intact. Therefore, the foil 18 is exposed to form connection portions 12 which provide metal to tissue contact for passage of current or measurement of voltage. The openings 28 expose the lead pads 10 and connection portions 12. The lead pads 10 are connected to respective connection portions 12 via covered paths 16.

Figure 6A:
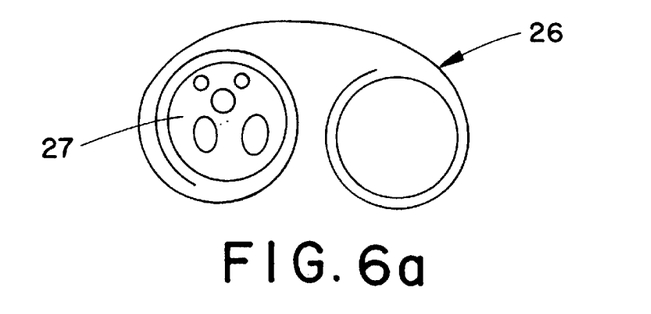
FIG. 6a is a graphic representation of an electrode structure which has been prestressed to form the structure with a curved surface.

A prestressing step I optionally forms the electrode structure 26 into a curved surface as shown in FIG. 6a. A curved surface is useful for conforming the electrode structure to an outside surface of a nerve or other similar structure 27.

Figure 6B:
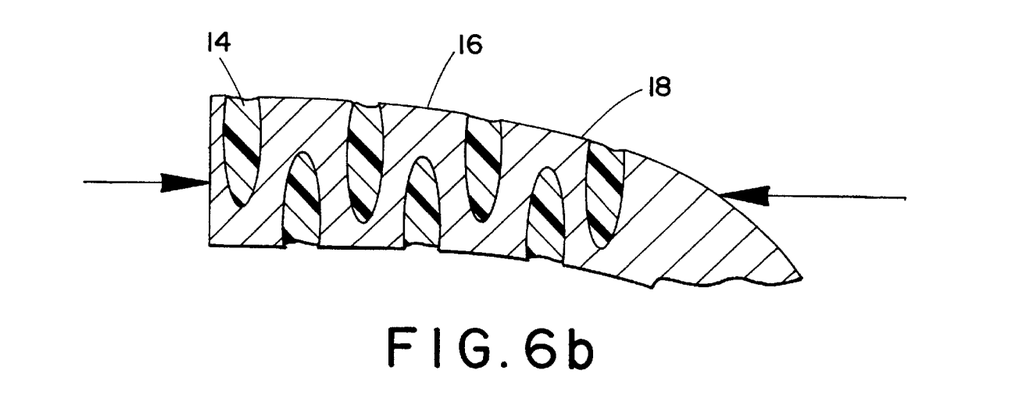
FIG. 6b is an enlarged elevational view of a portion of FIG. 1 with compression forces.

FIG. 6b shows a portion of the connection path 16. Arrows in FIG. 6b represent compressive forces experienced by the foil 18 when it is flexed. The holes cut in the metal foil 18, in conjunction with the polymer filling 14, allow the foil to flex without buckling when subjected to these compressive forces.

A second embodiment of the invention will be described with reference to FIGS. 2 and 7–11. The construction of the electrode structure begins with a sheet of metal foil 18.

Figure 7:
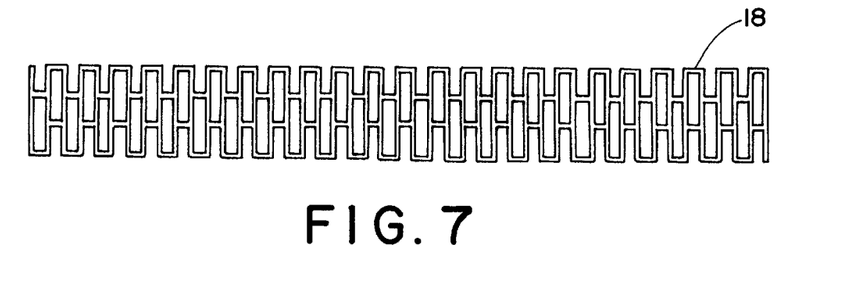
FIG. 7 is a top elevational view of the metal sheet having holes forming a mesh.
Figure 8:
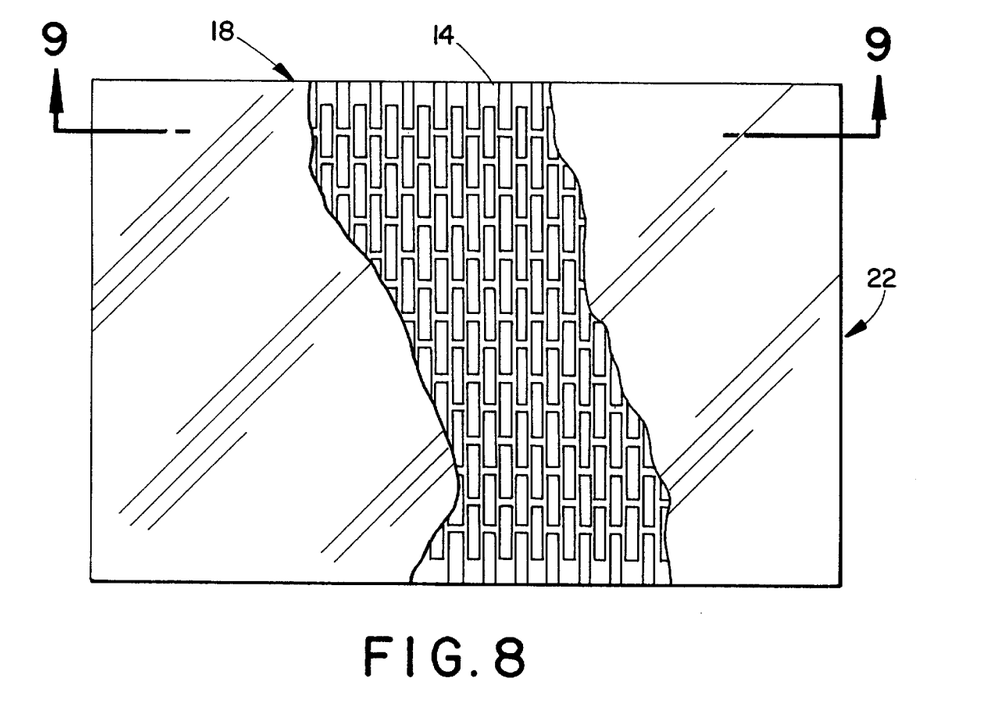
FIG. 8 is a top elevational view of a partially constructed electrode consisting of a metal sandwiched between two layers of a polymer.
Figure 9:
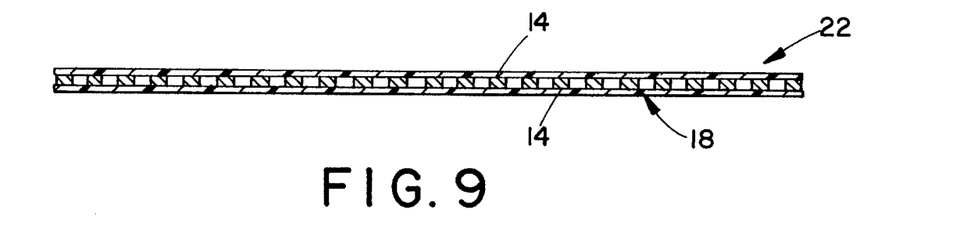
FIG. 9 is a cross-sectional side view of the polymer-metal-polymer structure shown in FIG. 8.

With reference to FIG. 2, holes are cut or etched into the foil 18 during the cutting step A to form a mesh pattern (see FIG. 7). The holes could be cut into rectangular, or other geometric circular shapes. After the holes are cut, residual internal stresses may optionally be removed from the foil 18 during the annealing step B.

Next, the laser cutable polymer 14 is introduced into the holes of the metal foil 18 in the filling step C. The laser cutable polymer 14 is preferably silicone rubber. However, other materials with similar qualities are also contemplated. The resulting metal-polymer combination is then sandwiched between two layers of the polymer 14 in the covering step D to form the polymer-metal-polymer structure 22 (see FIGS. 8 and 9). The metal layer of the resulting polymer-metal-polymer structure 22 is electrically conductive in both the X and Y planes.

Figures 10, 12:
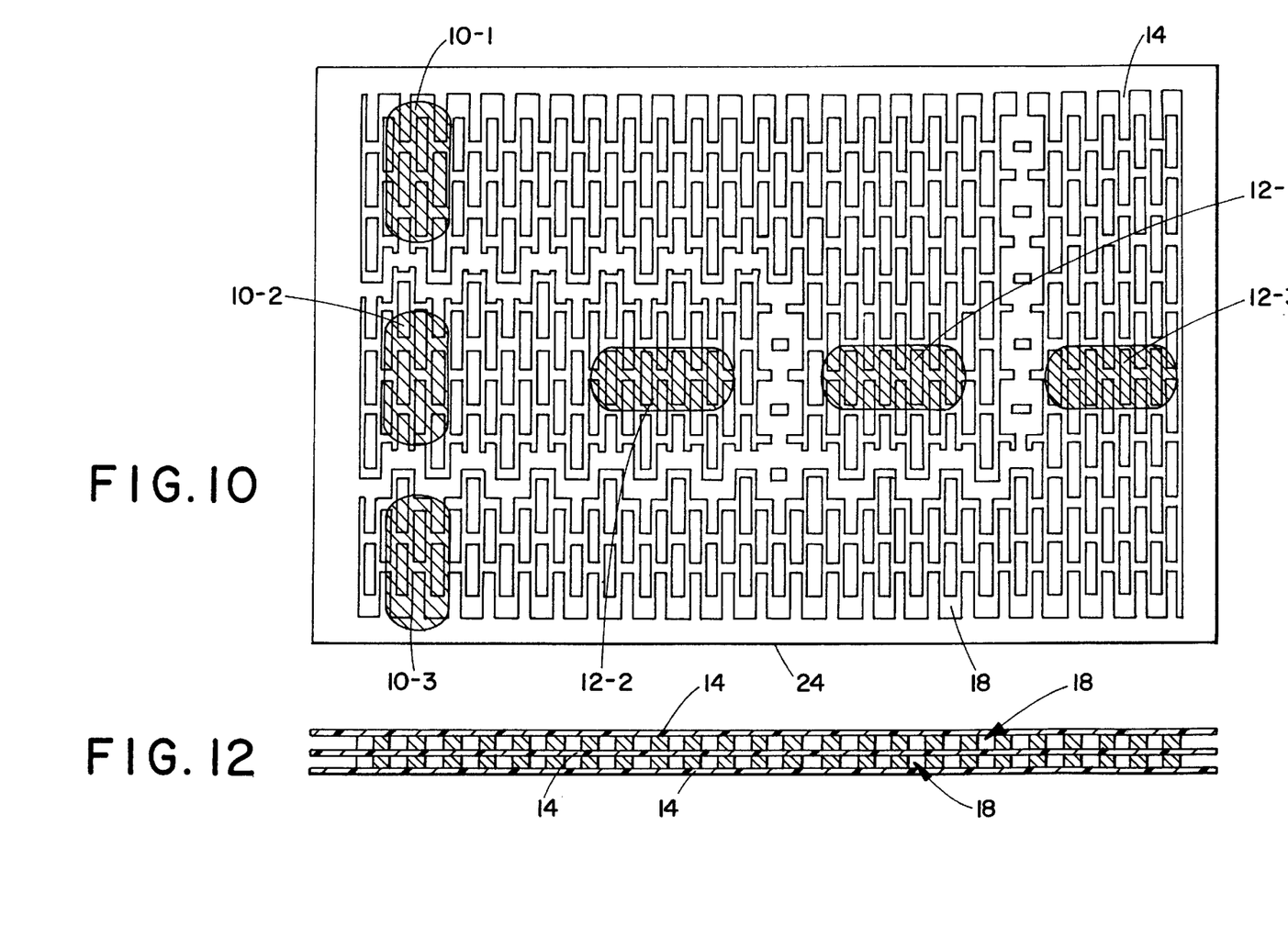

The tracing of desired electrodes is then formed from the polymer-metal-polymer structure 22 in the tracing step E (see FIG. 10). The cutting step F includes cutting holes through the tracing to create isolated regions of electrical conduction. The cutting is preferably done using a laser device.

To complete the construction of the electrode structure, the cut-out trace 24 is laminated in coating step G. The lead pads 10 and electrical connection portions 12 are created in the coated tracing in the create opening step H. Preferably, a laser cutting device is used to create the openings. A beam intensity of the laser is adjusted so that the laser cutting device cuts through the laminated layer and polymer layer while leaving the metal foil 18 intact. The foil 18 is exposed at the lead pads 10 and connection portions 12 to provide metal to tissue contact for passage of current or measurement of voltage. In FIG. 10, lead pad 10-1 and connector 12-1 are electrically connected to each other and electrically isolated from all other lead pads and connectors on the electrode structure. Similar connections exist between lead pads 10-2, 10-3 and connectors 12-2, 12-3, respectively.

Figure 11:
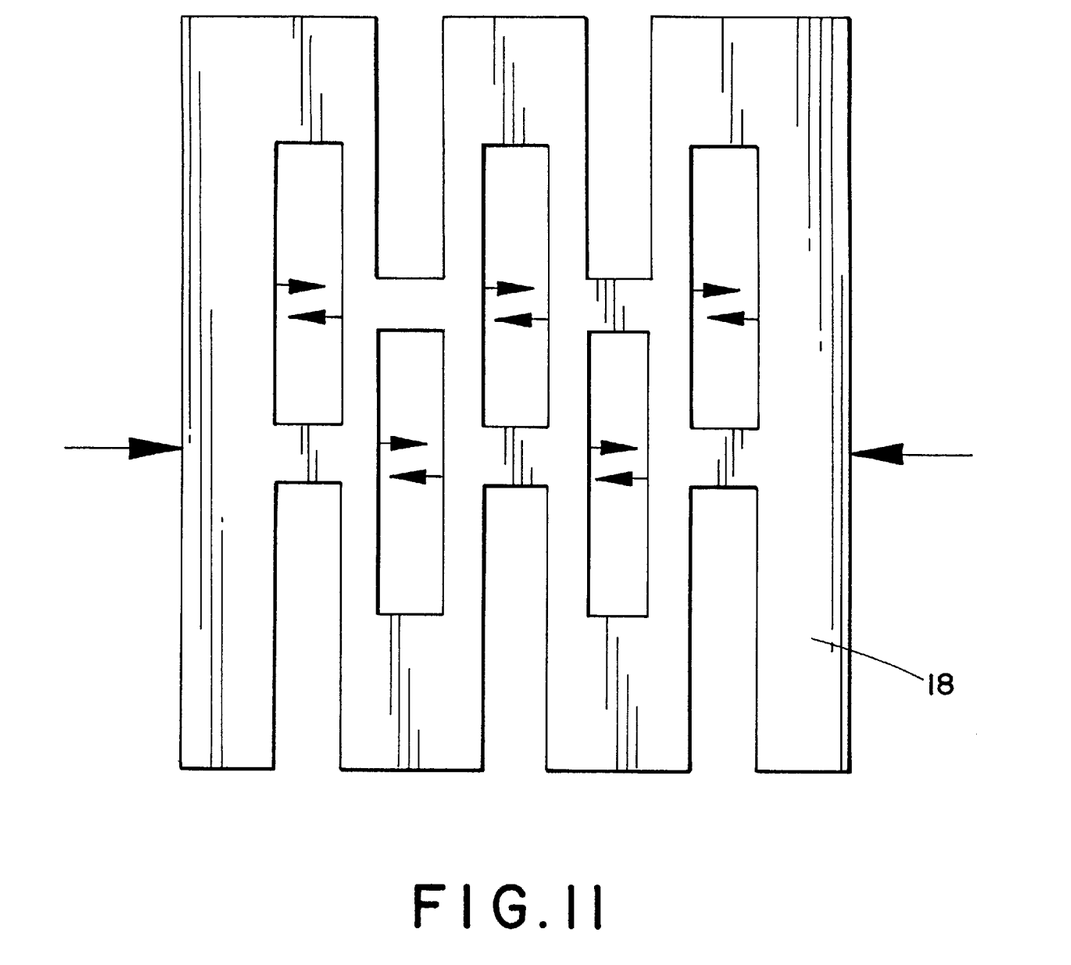
FIG. 11 is a top elevational view of a portion of FIG. 8 illustrating that longitudinal loads may be accommodated by the planar structure while avoiding buckling; and, FIG. 12 is a cross-sectional side view of a two-layer electrode structure.

FIG. 11 shows a portion of the foil mesh 18. Arrows in FIG. 11 represent compressive forces experienced by the foil mesh 18 when it is flexed. The holes cut in the foil mesh 18, in conjunction with the polymer filling 14, allow the foil to flex without buckling when subjected to these compressive forces.

FIG. 12 illustrates a two-layer electrode structure created by stacking two polymer-mesh-polymer structures on top of one another. Other multiple-layer electrode structures are also contemplated.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A neural stimulating electrode structure, comprising:
   a sheet of metal foil having a first face and a second face, with holes located within the metal foil, the holes formed in predetermined patterns allowing the metal foil to flex without buckling, metal foil between the holes defining a plurality of discrete electrodes on the metal foil when the foil is cut;
   a first polymeric base layer covering the first face of the metal foil;
   a second polymeric base layer covering the second face of the metal foil, the first and second polymeric base layers further filling the holes in the metal foil;
   a third polymeric base layer covering at least one of the first and second polymeric base layers; and
   external connection points, formed at locations where portions of the third polymeric base layer and one of the first and second polymeric base layers have been removed, each of the connection points corresponding to metal foil between a pair of holes associated with one of the discrete electrodes, at least one of the discrete electrodes at least one of contacting tissue, passing current and measuring voltage.

2. The neural stimulating electrode structure as set forth in claim 1 wherein:
   the three polymeric base layers include silicone rubber.

3. The neural stimulating electrode structure as set forth in claim 1 wherein:
   the three polymeric base layers are laser cutable.

4. The neural stimulating electrode structure as set forth in claim 1 wherein:
   the metal foil is annealed for removing residual internal stresses.

5. The neural stimulating electrode structure as set forth in claim 1 wherein:
   the metal foil has a thickness between about 10 $\mu$m and about 75 $\mu$m.

6. The neural stimulating electrode structure as set forth in claim 1 wherein:
   the neural stimulating electrode structure forms a curving surface for conforming to an outside surface of a neural tissue.

7. A neural stimulating electrode structure, comprising:
   a sheet of metal foil having a first face and a second face, with holes forming a mesh, the mesh allowing the metal foil to flex without buckling when subjected to compressive forces, the mesh also enabling electrical conduction in a first direction and a second direction across the metal foil, the metal foil mesh between the holes defining at least one electrically isolated region;
   a first polymeric base layer covering the first face of the metal foil;
   a second polymeric base layer covering the second face of the metal foil, the first and second polymeric base layers filling the holes defined by the mesh;
   a third polymeric base layer covering at least one of the first and second polymeric base layers; and
   external connection points, formed at locations where portions of the third polymeric base layer and one of the first and second polymeric base layers have been removed, wherein portions of the metal foil are exposed, the exposed metal foil portions corresponding to metal foil between a pair of holes, each pair of holes being associated with one of the electrically isolated regions on the metal foil.

8. The neural stimulating electrode structure as set forth in claim 7 wherein:
   the three polymeric base layers include silicone rubber.

9. The neural stimulating electrode structure as set forth in claim 7 wherein:
   the three polymeric base layers are laser cutable.

10. The neural stimulating electrode structure as set forth in claim 7 wherein:
    the metal foil is platinum foil having a thickness between about 10 $\mu$m and about 75 $\mu$m.

11. The neural stimulating electrode structure as set forth in claim 7 wherein:
    the metal foil is annealed for removing residual internal stresses.

12. The neural stimulating electrode structure as set forth in claim 7 wherein:
    the sheet of metal foil forms a curving surface for conforming to an outside surface of a tissue.

13. An electrode structure, comprising:
    a common structure including an electrically conductive material;
    at least one lead pad electrode formed within the common structure;
    at least one connection pad electrode formed within the structure;
    at least one conductive path formed within the common structure, each of the conductive paths defining an electrical connection between a unique one of the lead pad electrodes and a unique corresponding one of the connection pad electrodes, each of the conductive paths including a plurality of voids; and
    at least one non-conductive interconnection electrically isolating (i) each of the lead pad electrodes from each of the other lead pad electrodes, (ii) each of the connection pad electrodes from each of the other connection pad electrodes, (iii) each of the lead pad electrodes from each of the connection pad electrodes, and (iv) each of the conductive paths from at least one of the other conductive paths.

14. A method of manufacturing a neural stimulating electrode structure, comprising:
    forming holes into a metal foil sheet for forming patterns and allowing the metal foil to flex without buckling when subjected to compressive forces, segments of the metal foil between the holes defining a plurality of discrete electrodes;

filling the holes with a laser cutable polymer, the polymer accommodating the compressive forces;

sandwiching the metal foil between two layers of the polymer;

cutting the sandwiched metal foil to form at least one of the discrete electrodes within the metal foil, each of the discrete electrodes being electrically isolated from each of the other discrete electrodes;

covering the at least two discrete electrodes with a second coating of the polymer; and, creating one pair of openings for each of the at least two electrodes, one opening in each of the pairs of openings exposing a respective portion of the metal foil for interfacing the respective portion of the metal foil with one of tissue and an electrical lead.

15. The method of manufacturing a neural stimulating electrode structure according to claim 14, further including:

after the forming step and before the filling step, annealing the metal foil sheet for removing residual internal stresses.

16. The method of manufacturing a neural stimulating electrode structure according to claim 14, wherein the sandwiching step includes:

applying the polymer to a first face of the metal foil; and, applying the polymer to a second face of the metal foil.

17. The method of manufacturing a neural stimulating electrode structure according to claim 16, wherein after the step of cutting and before the step of creating, the method further includes:

forming the at least two electrodes into a curved surface for conforming to an outside surface of a neural tissue.

* * * * *